United States Patent [19]

Ruhenstroth-Bauer

[11] Patent Number: 5,589,461
[45] Date of Patent: Dec. 31, 1996

[54] ACTIVE SUBSTANCE FOR INHIBITING THE PROLIFERATION RATE OF HEPATOCYTES

[76] Inventor: G. Ruhenstroth-Bauer, Spitzelbergerstrasse 11, 82166 Gräfelfing, Germany

[21] Appl. No.: 243,873

[22] Filed: May 17, 1994

[51] Int. Cl.⁶ .............................. C07K 5/08; C07K 5/10; C07K 5/06
[52] U.S. Cl. ................................ 514/18; 514/12; 514/17; 514/21
[58] Field of Search .................................. 530/331; 514/18

[56] References Cited

U.S. PATENT DOCUMENTS 5,112,811  5/1992  Lenfant et al. ............................ 514/17

OTHER PUBLICATIONS

Cecil Textbook of Medicine 19th edition pp. 775–778, 786–796, 801–804 (1992).
J. Med. Chem. 1990, 33, 2122–2127, Synthesis and Activity of NAcSerAspLysPro Analogues on Cellular Interactions between T–Cell . . . Formation.
Cell Tissue Kinet (1990), 99–103, In vivo effect of the tetrapeptide, N–Acetyl–Ser–Asp–Lys–Pro, on the $G_1$–S transition of rate hepatocytes.

*Primary Examiner*—Howard E. Schain
*Assistant Examiner*—Patricia L. Touzeau
*Attorney, Agent, or Firm*—Jones, Tullar & Cooper, P.C.

[57]  ABSTRACT

A method of inhibiting the proliferation rate of hepatocytes in a subject by administering to the subject the free tripeptide of the composition SDK (serine-aspartic acid-lysine) or the salt thereof.

3 Claims, 2 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:1:

Ser Asp Lys Pro
1

ACTIVE SUBSTANCE FOR INHIBITING THE PROLIFERATION RATE OF HEPATOCYTES

BACKGROUND OF THE INVENTION

The present invention relates to an active substance for inhibiting the proliferation rate of hepatocytes.

The hepatocyte proliferation rate is normally very low in adult mammals. If, however, part of the liver is removed (partial hepatectomy) in young experimental animals, the proliferation rate suddenly increases by ten to twenty times its original value, dropping back to its normal value after having reached the previous original number of hepatocytes (i.e. after six to eight days). This course of development in liver regeneration (hepatopoiesis) has already been made the object of numerous studies.

Investigation into the molecular mechanism of this loop system resulted in identifying a plurality of growth promoting or inhibiting factors (cf. summary given in: MICHALOPOULOS, G.K., "Liver Regeneration: Molecular Mechanisms of Growth Control"; FASEB, J. 4 (1990), p. 176–187). One such growth promoting factor, which was isolated in the seventies, is the hormone hepatopoietin (cf/German patent specifications 28 14 981, 29 14 903, 30 37 600).

It was found subsequently that hepatopoietin is contained as well in the ascites of the rat hepatic tumor YOSHIDA AH 130 (S. VOGL et al., J. Hepatol. 11, suppl. 2 (1990) p. 118). According to this, it would appear that this hepatocyte tumor continuously produces its own proliferation hormone. Different studies showed that injection of extracts containing hepatopoietin in mice whose hepatocytes had been injured by galactosamine, results in additional impairment, the lethal dose 50 of galactosamine being thus decreased. Apparently an existing liver damage will be enhanced by hepatocyte proliferation.

It was further found that a factor very similar to hepatopoietin in the blood plasma of patients suffering from hepatic cancer or from chronic hepatitis can be detected (TOPIC, E. et al., Fresenius J. of Anal. Chemistry, 343 (1992), p. 132–133). This is in agreement with the fact that hepatic cancer is closely connected with hepatitis and hepatic cirrhosis (Okuda, K., Hepatol. 15 (1992), p. 948–963).

It is also known that the behaviour of human hepatocytes in tissue culture is very similar to that of animal cells (cf. ISMAIL, T. et al., J. Biol. Chem. 14 (1991), p. 1076–1082).

The search for a growth inhibitor involved in the above described hepatopoiesis loop system resulted in isolating the tetrapeptide N-Acetyl-Ser-Asp-Lys-Pro (N-Ac-SDKP; LOMBARD, M.-N. et al., Cell Tissue Kinet. 23 (1990), p. 99–103). The inhibiting effect, however, has been detected only in adult rats submitted to partial hepatectomy and in young animals (loc. cit.)

From publication DE 40 07 605 A1, the tripeptide Ser-Asp-Lys (corresponding to SDK in the nomenclature used hereinafter, cf. e.g. KARLSON, "Kurzes Lehrbuch der Biochemie", editors Georg Thieme Verlag Stuttgart, 12th edition, 1984, p. 23) is known. According to this, publication SDK inhibits rosette formation due to interaction of human T-cells (leukocytes) and sheep erythrocytes (cf. also THIERRY, J. et al., J. Med. Chem. 33 (1990), p. 2122–2127). Furthermore, an immunomodulating effect of SDK is described, namely stimulation of the humoral response (generation of IgM secreting B-lymphocytes) to red blood cells of sheep in mice.

There are, however, no indications as to any other effects of SDK.

SUMMARY OF THE INVENTION

It is an object of the invention to provide an active substance for inhibiting the present proliferation rate of hepatocytes. This active substance should inhibit hepatopoiesis after partial hepatectomy as well as the growth of hepatocyte tumors Accordingly, the present invention provides using the free tripeptide of the composition SDK (serine-aspartic acid-lysine) or a salt thereof for inhibiting the proliferation rate of hepatocytes.

The tripeptide can be prepared and used in its free form as a so-called dual ion (the COOH group acts as an acid, the $NH_3$ group acting as a base) as well as in the crystalline form as a salt of acetic acid, citric acid or an inorganic acid. A particularly well crystallizing salt is easier to purify and to dissolve.

Surprisingly, the tripeptide SDK, unlike the tetrapeptide SDKP, produces a strongly proliferation inhibiting effect already at low concentrations. It produces this effect not only in experiments with rats after partial hepatectomy, but also in YOSHIDA hepatic tumor cells. This means that hepatic tumor cells, inasmuch as they are a source of autocrine production of hepatopoietin, have their proliferation very strongly inhibited by the tripeptide SDK. In tissue cultures of human hepatoma cells it was possible to detect a significantly proliferation inhibiting effect as well as inhibition of the synthesis of hepatitis-B viruses. Moreover, the possible connection between hepatic cancer, hepatitis and hepatic cirrhosis supports the thesis that the tripeptide SDK might be active in all these diseases.

BRIEF DESCRIPTION OF THE DRAWINGS

In the following, experiments leading to the above mentioned results are described in further detail with reference to the attached drawings, in which.

DETAILED DESCRIPTION

Figure 1:
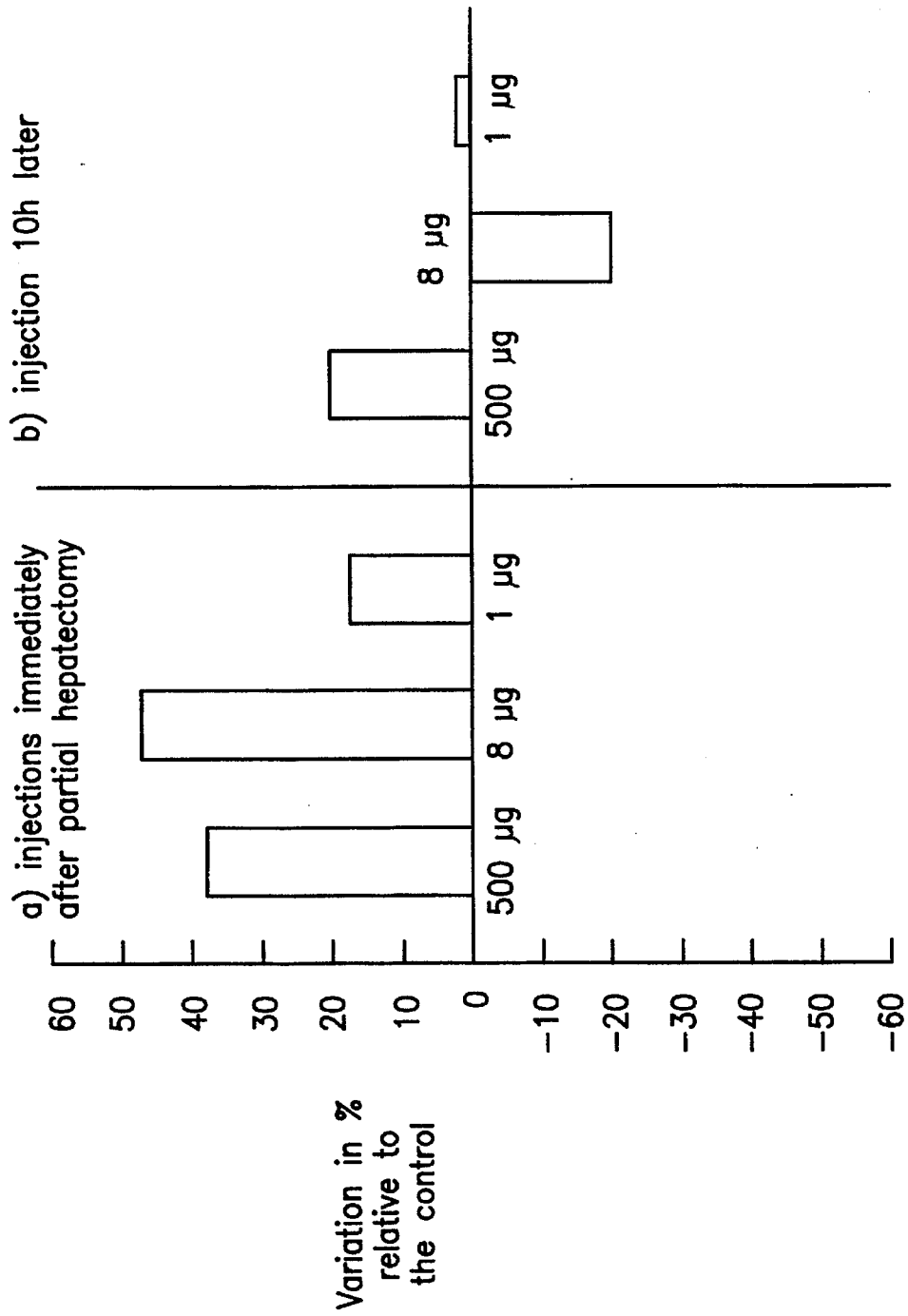
FIG. 1 is a graph showing the effect of the known tetrapeptide SDKP.

1. Influence of the known tetrapeptide SDKP on the proliferation rate of hepatocytes in rats after partial hepatectomy.

To carry out these experiments, young female Wistar rats weighing 100 g were used, which had been provided from the SPF animal house department of the Max-Planck-Instut für Biochemie in D-82152 Martinstied.

Seven groups of rats were subjected to 66% partial hepatectomy. In each experimental group 4 animals were used. In a slight modification of the Higgins and Anderson method (Higgins, G. M., Anderson, R. M., Afchives of Pathology 12 (1931), p. 186–202), the rats were submitted to partial hepatectomy between 13.00 h and 13.30 h. The tetrapeptide SDKP synthesized in the conventional way and dissolved in 1 ml of 0.9% NaCl was injected intraperitoneally (i.p.) to three groups immediately after operation and to three other groups 10 hrs after the operation, each three with different quantities (500 µg, 1 µg). The seventh group served as a control group, receiving the solvent only. After 19 hrs (starting from 8.00 h of the following day), 50 µl of 6-³H-thymidine (1.85 MBq) were administered to the rats i.p. Exactly one hour later, the animals were killed by means of diethyl ether (ether), and the residual liver was shock-frozen in liquid nitrogen. The livers were conserved at –20° C. up to the time of determining the specific radioactivity of the DNA in the hepatocyte nuclei.

This specific radioactivity was used as a marker for the proliferation behaviour of the hepatocytes: Thymidine is incorporated only in DNA (not e.g. in RNA), and significant DNA synthesis is effected only during cell proliferation. The specific radioactivity of the DNA (in dpm/µg DNA) is the quotient of the result of radioactivity measurement of a sample (in dpm, i.e. disintegrations per minute) by the DNA content of that sample (in µg). The proliferation promoting or proliferation inhibiting character of the peptide (depending on the administered dose and the time of administration after partial hepatectomy) was determined by establishing the percentage of the specific radioactivity of the DNA in the hepatocyte nuclei of the experimental group as compared with the specific radioactivity of the control group associated with each experiment.

For determination of the specific radioactivity, the DNA was first extracted from the liver. For this purpose, each liver was pottered (12 impacts/1200 rpm), i.e. homogenized, with seven times its quantity of a saccharose solution (0.32 M saccharose, 3 mM $MgCl_2$, pH 7.3). After filtration through a 150 µm gauze filter, 1 ml of the homogenate were centrifuged in the minifuge (Heraeus-Christ, Osterrode/Harz) at 800 rpm (120×g). The supernatant was discarded. The pellet was incorporated into 200 µl of the saccharose solution and transferred into an Eppendorf tube. Then 1 ml of a 60% saccharose solution was added and centrifuged for 5 min in an Eppendorf centrifuge. The supernatant was discarded. The pellet was suspended in 3×1 ml of 0.25M perchloracetic acid (PCA) and transferred into a glass tube. Then it was cooled at 4° C. for at least 30 min. This was followed by centrifuging in the minifuge at maximum rpm ($V_{max}$) for 15 min, and the supernatant was discarded. 1 ml of 0.5 M NaOH was added to the pellet, and it was shaken at room temperature for 30 min. Then it was mixed for a short time, and the contents were divided up in two tubes. 4.5 ml of 0.5 M PCA were added to each 0.5 ml (i.e. to each tube - 1 tube being kept in reserve). The samples were maintained at 4° C. for at least 30 min (or overnight) and then centrifuged in the minifuge at maximum rpm ($V_{max}$) for 15 min. The supernatant was discarded. 3 ml of 0.5 M PCA were added to each pellet, and it was boiled in the water bath at 95° C. for 20 min. After centrifuging again, both supernatants were combined into one sample and mixed.

For measurement of the radioactivity, scintillation counting liquid was added to 1 ml of the extract, and ³H measurement was effected. The DNA content of the extract was established according to the Burton method (Burton, K., Biochem. 62 (1956), p. 315–323). To prepare the color reaction mixture, 1.5 g of diphenylamine were dissolved with a small quantity of glacial acetic acid, and 1.5 ml of $H_2SO_4$ were added. Then it was replenished with glacial acetic acid to make 100 ml. Shortly before using it, 0.5 ml of an acetaldehyde solution were added. For preparing the acetaldehyde solution, 2 ml of acetaldehyde were replenished with $H_2O_{dest}$ at 4° C. to make 100 ml. 1 ml of the color reaction liquid was added to 0.5 ml of the extract. Then the samples were stored in the dark at room temperature and measured at 590 nm after 22–24 hrs.

For measurements of radioactivity as well as of DNA, three parallel measurements were effected for each sample.

The analysis given in FIG. 1 shows that the known tetrapeptide SDKP has a strongly proliferation promoting effect if it is injected immediately after operation (between 20 and 50%). When injected 10 hrs after the operation, it has a proliferation promoting effect if large quantities (500 µg) are administered, while small quantities (8 µg) are slightly proliferation inhibiting, and still smaller quantities (e.g. 1 µg) virtually not at all (cf. FIG. 1).

2. Influence of the tripeptide SDK according to the present invention on the proliferation rate of hepatocytes in rats after partial hepatectomy.

Six groups of rats were submitted to 66% partial hepatectomy. 1 µg of tripeptide SDK synthesized in the conventional way and dissolved in 1 ml of 0.9% NaCl was injected in each animal: in the first group immediately after operation, and in other groups 1 h, 3 hrs 6 hrs and 10 hrs respectively after the operation. The sixth group served as a control group, receiving only the solvent. The sequence of manipulations was identical with the one described in item 1.

Figure 2:
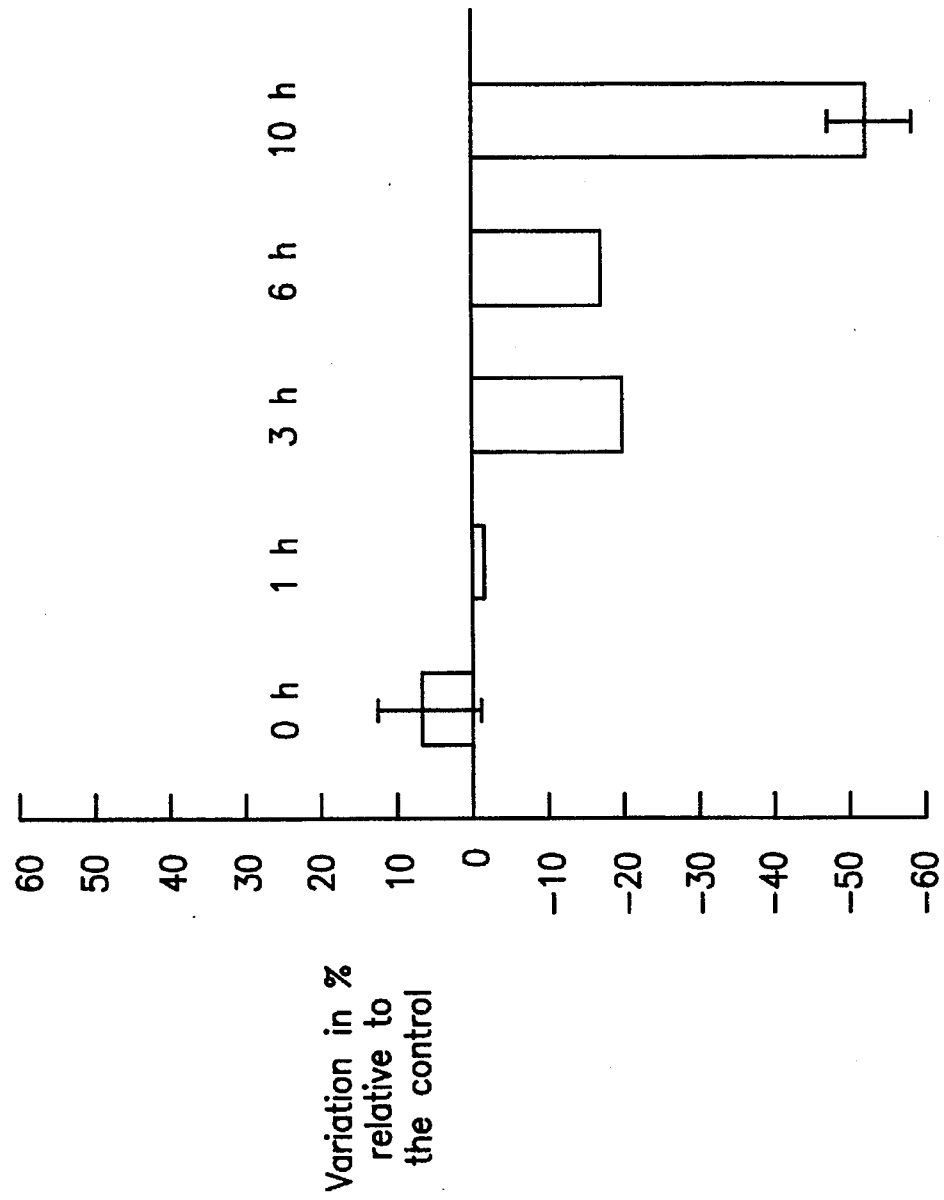
FIG. 2 is a graph showing the effect of the tripeptide according to the present invention.

The analysis given in FIG. 2 shows that, though the tripeptide SDK has a slightly proliferation promoting effect when injected immediately after operation, there is an inhibiting effect if the injection is administered after a certain time interval, the inhibiting effect increasing with increasing length of that interval. Ten hours after operation, the decrease in proliferation is about fifty percent (cf. FIG. 2).

A comparison of these two figures clearly shows the surprisingly different effects of the tetrapeptide SDKP and of the tripeptide SDK on the hepatocyte proliferation rate in rat after partial hepatectomy. The tripeptide SDK has a practically proliferation inhibiting effect, i.e. already in extremely low concentrations.

3. Influence of the tripeptide SDK on the development of the YOSHIDA ascites AH 130 in rat.

Two groups, each comprising five female Wistar rats weighing approx. 100 grams, were inoculated with the YOSHIDA liver tumor cell ascites AH 130 of a rat having been infected 8 days ago. 0.5 ml of ascites fluid were injected intraperitoneally (i.p.) to each animal. Starting on the seventh day after ascites inoculation, 1 µg of SDK (dissolved in 1 ml of 0.9% NaCl solution) was injected i.p. to each animal of one group (five rats) during four days. Then the animals of both groups were killed. The following parameters were determined:

(a) Weight or respectively volume of ascites fluid. The killed rats were weighed, the ascites was sucked off as completely as possible, and the animals were weighed again. The difference resulting from these two ponderations corresponded to the ascites volume (1 g ≈1 ml).

(b) Number of tumor cells in the ascites 2 ml of the sucked-off ascites for each animal were placed into an EDTA tube, to prevent cells from agglomerating. With an aliquot thereof, the number of tumor cells was measured in a Coulter counter and extrapolated for the total volume.

The results are listed in the following chart. The first column shows the volume of ascites fluid as the difference between the weights of rats prior and subsequently to sucking off, but after deduction of the 2 ml required for measuring the number of cells. The third and fourth columns give the respective results of twin measurements.

| Rat Nr. | Weight of rat | Ascites in ml | Cell number measured ($10^9$/l) | Cell number total × $10^6$ | Mean value + standard deviation |
|---|---|---|---|---|---|
| | | | without SDK | (control) | 774.2 ± 176.7 |
| 1 | 140 | 39 | 22.4 | 873.6 | |
| | 103 | | 19.0 | 741.0 | |
| | 37 | | | | |
| 2 | 139.8 | 37.6 | 18.0 | 676.8 | |
| | 104.2 | | 24.6 | 925.0 | |
| | 35.6 | | | | |
| 3 | 144.1 | 43.6 | 23.0 | 1002.8 | |
| | 102.5 | | 23.5 | 1024.6 | |
| | 41.6 | | | | |
| 4 | 126.2 | 19.1 | 27.4 | 523.3 | |
| | 109.1 | | 28.7 | 548.2 | |
| | 17.1 | | | | |
| 5 | 136.7 | 32.5 | 22.8 | 741.0 | |
| | 106.2 | | 21.1 | 685.7 | |
| | 30.5 | | | | |
| | | | with SDK (1 µg/animal) | | 147.7 ± 70.1 |
| 6 | 96.8 | 5.1 | 4.7 | 24.0 | |
| | 93.7 | | 3.4 | 17.3 | |
| | 3.1 | | | | |
| 7 | 110.9 | 5.2 | 42.3 | 220.0 | |
| | 107.7 | | 38.1 | 198.1 | |
| | 3.2 | | | | |
| 8 | 122.2 | 5.1 | 33.5 | 170.8 | |
| | 119.1 | | 36.7 | 187.2 | |
| | 3.1 | | | | |
| 9 | 97.3 | 4.3 | 36.2 | 155.7 | |
| | 95.0 | | 35.7 | 153.5 | |
| | 2.3 | | | | |
| 10 | 91.6 | 5.7 | 33.2 | 189.2 | |
| | 87.9 | | 28.3 | 161.3 | |
| | 5.7 | | | | |

Comparison of the results shows that:

There is a drastic decrease of the total number of tumor cells as well as of the quantity of ascites.

The average number of tumor cells in rats treated with the tripeptide SDK is only 19.1% of the number found in control animals.

4. Influence of the tripeptide SDK on human tumor cells in tissue culture.

The effect of the tripeptide on human tumor cells was tested in an in-vitro model. For this purpose, Hep G2 cells were used. This cell line is a human hepatom from the tumor cell bank of "Deutsches Krebsforschungszentrum Heidelberg", which is cultivated as a monolayer in 90% DMEM (Dulbecco's modified Eagle's medium)/10% FKS (fetal calf serum) in a subculture interval of three to five days. Sixty dishes of each of the experimental and control cultures were used. A solution of 20 mg of SDK in 0.2 ml of 0.9% NaCl served as a stock solution which was diluted with a physiological sodium chloride solution as required for each case.

One day after transferring the cells, 0.2 ml of tripeptide SDK dissolved in 0.9% NaCl (concentration: 1 µg/ml) were added to each 10 ml of culture medium. The control dishes received 0.2 ml of solvent. Thereby a five to ten percent inhibition of cell growth was observed in the experimental dishes as compared with the control dishes.

This proves a significant effect of the tripeptide SDK also on human cells.

This test was repeated, this time adding 0.5 ng, 1.0 ng, 2.0 ng and 4.0 ng of SDK in 0.9% NaCl per 1 ml of culture medium. The control dishes again received the corresponding quantity of solvent. Moreover, 0.05 mCi 6-$^3$H-thymidine were added to the cultures 24 hrs prior to expiration of the observation period, followed by incubation for 1 hour. The DNA of the cells was isolated as described under item (1.), and the radioactivity was measured. The results are listed in the following chart.

| ng of SDK per ml of medium | Radioactivity in dpm/mg DNA | Inhibition of proliferation in % |
|---|---|---|
| 0 (control) | 9874 ± 429 | — |
| 0.5 | 7968 ± 1096 | 19.3 |
| 1.0 | 6065 ± 4809 | 44.9 |
| 2.0 | 6722 ± 296 | 34.0 |
| 4.0 | 7833 ± 1102 | 12.4 |

In this experiment, in which the concentration of SDK was significantly lower than 20 ng/ml of culture medium, the differences are still more obvious. Accordingly there exists an efficacy-concentration window, i.e. at a concentration of 1 ng/ml of culture medium, SDK has its maximum proliferation inhibiting effect.

5. Influence of the tripeptide SDK on the synthesis of hepatitis B viruses in human liver tumor cells in tissue culture.

Hepatitis B viruses can be cultivated in Hep G2 cells. For this purpose, a recombining plasmide containing the complete virus DNA is channelled into the cells. Starting from this, the synthesizing mechanism of the cells transfected in this way will produce hepatitis B viruses (cf. Chungming Chang et al., EMBO J. 6, p. 675–680, 1987) The virus synthesis manifests itself by secreting large quantities of two surface antigens of that virus (HBSAG and HBEAG). The antigens can be detected by means of a radioimmunoassay (RIA). In this determination, an unknown quantity of antigen (HBSAG and HBEAG) competes with a known quantity of radioactively marked antigen for a limited number of antibody binding positions in a predetermined quantity of the antiserum. In the state of equilibrium, the surplus antigen exists in both the bound and the free dissolved conditions. Now, if the quantity of radioactively marked antigen is constant in a series of reactions, the proportion bound to the antibody will decrease in accordance with an increasing quantity of unmarked antigen added to the individual samples.

For practical execution of this process, a calibration curve is established first, using known quantities of marked and unmarked antigen, which will then permit determination of the unknown quantity of antigen. After incubation, the free antigen is separated from the bound antigen, and the two fractions are measured separately.

A Hep-G2 cell culture was steadily transfected with hepatitis B viruses as described by SELLS et al., Proc. Natl. Acad. Sci. USA 1987, 84, p. 1005–1009. The transfected cells were sowed in ten 4.5 cm dishes at a density of 8×$10^5$ cells, and in four 9 cm dishes at a density of 1.6×$10^6$ cells respectively. After 24 hours, fresh medium was added, containing the tripeptide SDK at concencentrations of 0.5 ng/ml, 1.0 ng/ml, 3.0 ng/ml and 5 ng/ml for each two 4.9 cm dishes, or 1.0 ng/ml for each two 9 cm dishes respectively. The tripeptide had been prediluted in completed DMEM (1 g/ml) and sterilized by filtration. The remaining dishes served as a control, receiving the pure medium. The old medium was conserved in the supernatant for measurement of antigens, in order to exclude artifacts due to possible heterogeneities of cell density. The samples of medium for measurement of antigens were taken after six days. Measurement was effected using a standard RIA kit (HBSAG Ansria II/125, type 7802, and HBEAG Abbott Hbe (rDNA), type 1237/24, both from Abbott, Wiesbaden), according to instructions for use. The experiments were conducted with twin samples (two dishes each), since the cells from one dish were not enough. The results are listed in the following chart.

| Dish | ng of SDK per ml of medium | Ratio of mean values in cpm before/after treatment | |
|---|---|---|---|
| | | HBSAG | HBEAG |
| 4.5 cm: | | | |
| 1, 2 | untreated | 4.70 | 7.50 |
| 3, 4 | 0.5 | 4.47 | 6.10 |
| 5, 6 | 1.0 | 4.18 | 6.22 |
| 7, 8 | 3.0 | 4.57 | 7.31 |
| 9,10 | 5.0 | 4.18 | 8.00 |
| 9.0 cm: | | | |
| 11, 12 | untreated | 4.37 | 8.07 |
| 13, 14 | 1.0 | 3.89 | 6.59 |

The concentration of antigens, and hence the virus synthesis is significantly reduced. Here again, it appears that the tripeptide SDK has its highest efficiency at a concentration of 0.5 to 1 ng/ml of culture medium.

---

---

We claim:

1. A method of inhibiting the proliferation rate of hepatocytes in a subject, comprising the step of:
administering the free tripeptide of the composition SDK (serine-aspartic acid-lysine) or the salt thereof for treating the subject by administering a therapeutically effective amount to a subject in need thereof.

2. The method of claim 1, wherein the free tripeptide is administered in the treatment of hepatic cancer.

3. The method of claim 1, wherein the free tripeptide is administered after partial hepatectomy.

* * * * *